(12) United States Patent  (10) Patent No.: US 8,298,150 B2
Mann et al.  (45) Date of Patent: Oct. 30, 2012

(54) HEMODYNAMIC WAVEFORM-BASED DIAGNOSIS AND TREATMENT

(75) Inventors: Brian Mann, Beverly Hills, CA (US); James S. Whiting, Los Angeles, CA (US); Neal L. Eigler, Pacific Palisades, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 1813 days.

(21) Appl. No.: 11/520,454

(22) Filed: Sep. 13, 2006

(65) Prior Publication Data

US 2007/0088223 A1   Apr. 19, 2007

Related U.S. Application Data

(63) Continuation-in-part of application No. 10/698,031, filed on Oct. 29, 2003, now Pat. No. 7,483,743, which is a continuation-in-part of application No. 10/127,227, filed on Apr. 19, 2002, now Pat. No. 7,115,095, which is a continuation of application No. 09/956,596, filed on Sep. 19, 2001, now abandoned, which is a continuation of application No. 09/481,084, filed on Jan. 11, 2000, now Pat. No. 6,328,699.

(60) Provisional application No. 60/470,468, filed on May 13, 2003, provisional application No. 60/716,611, filed on Sep. 13, 2005.

(51) Int. Cl.
*A61B 5/02* (2006.01)
*A61B 5/04* (2006.01)

(52) U.S. Cl. ......... 600/485; 600/486; 600/513; 600/509

(58) Field of Classification Search .................. 600/481, 600/483–485, 486, 488, 508, 509, 513
See application file for complete search history.

(56) References Cited

U.S. PATENT DOCUMENTS

| | | | |
|---|---|---|---|
| 3,672,352 A | 6/1972 | Summers | |
| 4,038,990 A | 8/1977 | Thompson | |
| 4,535,774 A | 8/1985 | Olson | |
| 4,679,144 A | 7/1987 | Cox et al. | |
| 4,710,164 A | 12/1987 | Levin et al. | |

(Continued)

FOREIGN PATENT DOCUMENTS

EP   0472411   2/1992

(Continued)

OTHER PUBLICATIONS

Steinhaus, David M et al., Initial Experience with an Implantable Hemodynamic Monitor, Circulation, vol. 93, No. 4, pp. 745-752, Feb. 15, 1996.

(Continued)

*Primary Examiner* — Navin Natnithithadha
(74) *Attorney, Agent, or Firm* — Knobbe, Martens, Olson & Bear, LLP (57) ABSTRACT

A method of monitoring pressure within a medical patient, includes measuring an actual pressure in a medical patient in a first time period; measuring an indicator of the actual pressure in the first time period, wherein the indicator is derived from an electrical signal of the patient's heart; determining a correlative relationship between the actual pressure and the indicator, wherein both the actual pressure and the indicator are obtained in the first time period; measuring the indicator in a second time period; and determining the actual pressure in the second time period based on the correlative relationship obtained in the first time period and the indicator obtained in the second time period.

13 Claims, 9 Drawing Sheets

U.S. PATENT DOCUMENTS

| | | |
|---|---|---|
| 4,718,891 A | 1/1988 | Lipps |
| 4,830,006 A | 5/1989 | Haluska et al. |
| 4,873,987 A | 10/1989 | Djordjevich et al. |
| 4,899,751 A | 2/1990 | Cohen |
| 4,899,752 A | 2/1990 | Cohen |
| 4,899,758 A | 2/1990 | Finkelstein et al. |
| 4,967,749 A | 11/1990 | Cohen |
| 4,984,572 A | 1/1991 | Cohen |
| 5,003,976 A | 4/1991 | Alt |
| 5,054,485 A | 10/1991 | Cohen |
| 5,103,828 A | 4/1992 | Sramek |
| 5,105,810 A | 4/1992 | Collins et al. |
| 5,113,869 A | 5/1992 | Nappholz et al. |
| 5,119,813 A | 6/1992 | Cohen |
| 5,129,394 A | 7/1992 | Mehra |
| 5,139,020 A | 8/1992 | Koestner et al. |
| 5,142,484 A | 8/1992 | Kaufman et al. |
| 5,156,148 A | 10/1992 | Cohen |
| 5,163,429 A | 11/1992 | Cohen |
| 5,184,614 A | 2/1993 | Collins et al. |
| 5,188,106 A | 2/1993 | Nappholz et al. |
| 5,190,528 A | 3/1993 | Fonger et al. |
| 5,305,745 A | 4/1994 | Zacouto |
| 5,314,418 A | 5/1994 | Takano et al. |
| 5,324,327 A | 6/1994 | Cohen |
| 5,330,505 A | 7/1994 | Cohen |
| 5,368,040 A | 11/1994 | Carney |
| 5,372,607 A | 12/1994 | Stone et al. |
| 5,391,190 A | 2/1995 | Pederson et al. |
| 5,398,692 A | 3/1995 | Hickey |
| 5,409,009 A | 4/1995 | Olson |
| 5,417,717 A | 5/1995 | Salo et al. |
| 5,464,434 A | 11/1995 | Alt |
| 5,498,524 A | 3/1996 | Hall |
| 5,535,752 A | 7/1996 | Halperin et al. |
| 5,653,735 A | 8/1997 | Chen et al. |
| 5,690,611 A | 11/1997 | Swartz et al. |
| 5,693,075 A | 12/1997 | Plicchi et al. |
| 5,700,283 A | 12/1997 | Salo |
| 5,704,352 A | 1/1998 | Tremblay et al. |
| 5,743,267 A | 4/1998 | Nikolic et al. |
| 5,749,900 A | 5/1998 | Schroeppel et al. |
| 5,749,909 A | 5/1998 | Schroeppel et al. |
| 5,752,976 A | 5/1998 | Duffin et al. |
| 5,758,652 A | 6/1998 | Nikolic |
| 5,782,898 A | 7/1998 | Dahl et al. |
| 5,792,194 A | 8/1998 | Morra |
| 5,861,018 A | 1/1999 | Feierbach |
| 5,904,708 A | 5/1999 | Goedeke |
| 5,919,210 A | 7/1999 | Lurie et al. |
| 5,921,935 A | 7/1999 | Hickey |
| 5,935,158 A | 8/1999 | Holmstrom et al. |
| 5,954,752 A | 9/1999 | Mongeon et al. |
| 6,024,704 A | 2/2000 | Meador et al. |
| 6,035,233 A | 3/2000 | Schroeppel et al. |
| 6,074,345 A | 6/2000 | van Oostrom et al. |
| 6,112,116 A | 8/2000 | Fischell et al. |
| 6,152,885 A | 11/2000 | Taepke |
| 6,208,900 B1 | 3/2001 | Ecker et al. |
| 6,223,081 B1 | 4/2001 | Kerver |
| 6,223,087 B1 | 4/2001 | Williams |
| 6,234,973 B1 | 5/2001 | Meador et al. |
| 6,272,377 B1 | 8/2001 | Sweeney et al. |
| 6,272,379 B1 | 8/2001 | Fischell et al. |
| 6,277,078 B1 | 8/2001 | Porat et al. |
| 6,309,350 B1 | 10/2001 | VanTassel et al. |
| 6,317,626 B1 | 11/2001 | Warman |
| 6,328,699 B1 | 12/2001 | Eigler et al. |
| 6,360,123 B1 | 3/2002 | Kimchi et al. |
| 6,381,493 B1 | 4/2002 | Stadler et al. |
| 6,406,426 B1 | 6/2002 | Reuss et al. |
| 6,409,674 B1 | 6/2002 | Brockway et al. |
| 6,438,407 B1 | 8/2002 | Ousdigian et al. |
| 6,480,744 B2 | 11/2002 | Ferek-Petric |
| 6,501,983 B1 | 12/2002 | Natarajan et al. |
| 6,508,771 B1 | 1/2003 | Padmanabhan et al. |
| 6,553,263 B1 | 4/2003 | Meadows et al. |
| 6,558,351 B1 | 5/2003 | Steil et al. |
| 6,580,946 B2 | 6/2003 | Struble |
| 6,645,153 B2 | 11/2003 | Kroll et al. |
| 6,714,811 B1 | 3/2004 | Padmanabhan et al. |
| 6,760,628 B2 | 7/2004 | Weiner et al. |
| 6,804,558 B2 | 10/2004 | Haller et al. |
| 6,832,113 B2 | 12/2004 | Belalcazar |
| 6,970,742 B2 | 11/2005 | Mann et al. |
| 7,027,866 B2 | 4/2006 | Warkentin |
| 7,115,095 B2 | 10/2006 | Eigler et al. |
| 7,127,290 B2 | 10/2006 | Girouard et al. |
| 7,137,953 B2 | 11/2006 | Eigler et al. |
| 7,139,609 B1 | 11/2006 | Min et al. |
| 7,149,773 B2 | 12/2006 | Haller et al. |
| 7,181,283 B2 | 2/2007 | Hettrick et al. |
| 7,181,505 B2 | 2/2007 | Haller et al. |
| 7,277,745 B2 | 10/2007 | Natarajan et al. |
| 7,410,467 B2 | 8/2008 | Cooper |
| 7,483,743 B2 | 1/2009 | Mann et al. |
| 7,488,290 B1 | 2/2009 | Stahmann et al. |
| 7,590,449 B2 | 9/2009 | Mann et al. |
| 7,616,991 B2 | 11/2009 | Mann et al. |
| 2002/0013613 A1 | 1/2002 | Haller et al. |
| 2002/0022785 A1 | 2/2002 | Romano |
| 2003/0055344 A1 | 3/2003 | Eigler et al. |
| 2003/0055345 A1 | 3/2003 | Eigler et al. |
| 2003/0055461 A1 | 3/2003 | Girouard et al. |
| 2003/0139785 A1 | 7/2003 | Riff et al. |
| 2003/0199813 A1 | 10/2003 | Struble |
| 2004/0019285 A1 | 1/2004 | Eigler et al. |
| 2004/0106874 A1 | 6/2004 | Eigler et al. |
| 2004/0116992 A1 | 6/2004 | Wardle et al. |
| 2004/0147969 A1 | 7/2004 | Mann et al. |
| 2005/0080460 A1 | 4/2005 | Wang et al. |
| 2005/0136385 A1 | 6/2005 | Mann et al. |
| 2005/0165456 A1 | 7/2005 | Mann et al. |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0009810 A1 | 1/2006 | Mann et al. |
| 2006/0079793 A1 | 4/2006 | Mann et al. |
| 2006/0149330 A1 | 7/2006 | Mann et al. |
| 2006/0149331 A1 | 7/2006 | Mann et al. |
| 2007/0032831 A1 | 2/2007 | Eigler et al. |

FOREIGN PATENT DOCUMENTS

| | | |
|---|---|---|
| EP | 1050265 | 11/2000 |
| EP | 1057448 | 12/2000 |
| WO | WO 96/11722 | 4/1996 |
| WO | WO 99/56812 | 11/1999 |
| WO | WO 2004/066814 | 8/2004 |

OTHER PUBLICATIONS

Soufer, Robert, Treating a Sick Heart, Heart Disease, Nova Online web page (copyright 1997, WGBH).

Neergaard, Lauran, Internet assists in daily heart monitoring, CNN.com health web page: Feb. 22, 2000, (copyright 2000, Cable News Network).

Lowry, Fran, Heart failure patients, doctors linked in cyberspace, online article at www.theheart.org, Sep. 14, 2000.

Bailey, Steve, Device Tracks Ailing Hearts, online article at www.enquirer.com, Aug. 24, 2000.

*Right Atrial Pressure Waveforms*

FIG. 6A

Low mean atrial pressure
 1. Hypovolemia
 2. Improper zeroing of the transducer
Elevated mean atrial pressure
 1. Intravascular volume overload states
 2. Right ventricular failure due to valvular disease (tricuspid or pulmonic stenosis or regurgitation)
 3. Right ventricular failure due to myocardial disease (right ventricular ischemia, cardiomyopathy)
 4. Right ventricular failure due to left heart failure (mitral stenosis/regurgitation, aortic stenosis/regurgitation, cardiomyopathy, ischemia)
 5. Right ventricular failure due to increased pulmonary vascular resistance (pulmonary embolism, chronic obstructive pulmonary disease, primary pulmonary hypertension)
 6. Pericardial effusion with tamponade physiology
 7. Obstructive atrial myxoma
Elevated a wave (any increase to ventricular filling)
 1. Tricuspid stenosis
 2. Decreased ventricular compliance due to ventricular failure, pulmonic valve stenosis, or pulmonary hypertension
Cannon a wave
 1. Atrial-ventricular asynchrony (atria contract against a closed tricuspid valve, as during complete heart block following premature ventricular contraction, during ventricular tachycardia, with ventricular pacemaker)
Absent a wave
 1. Atrial fibrillation or atrial standstill
 2. Atrial flutter
Elevated v wave
 1. Tricuspid regurgitation
 2. Right ventricular heart failure
 3. Reduced atrial compliance (restrictive myopathy)
a wave equal to v wave
 1. Tamponade
 2. Constrictive pericardial disease
 3. Hypervolemia
Prominent x descent
 1. Tamponade
 2. Subacute constriction and possibly chronic constriction
 3. Right ventricular ischemia with preservation of atrial contractility
Prominent y descent
 1. Constrictive pericarditis
 2. Restrictive myopathies
 3. Tricuspid regurgitation
Blunted x descent
 1. Atrial fibrillation
 2. Right atrial ischemia
Blunted y descent
 1. Tamponade
 2. Right ventricular ischemia
 3. Tricuspid stenosis
Miscellaneous abnormalities
 1. Kussmaul's sign (inspiratory rise or lack of decline in right atrial pressure)-constrictive pericarditis, right ventricular ischemia
 2. Equalization ($\leq 5$ mm Hg) of mean right atrial, right ventricular diastolic, pulmonary artery diastolic, pulmonary capillary wedge, and pericardial pressures in tamponade
 3. M or W patterns: right ventricular ischemia, pericardial constriction, congestive heart failure
 4. Ventricularization of the right atrial pressure: severe tricuspid regurgitation
 5. Saw tooth pattern: atrial flutter
 6. Dissociation between pressure recording and intracardiac ECG: Ebstein's anomaly

*Left Atrial Pressure/Pulmonary Capillary Wedge Pressure Waveforms*

Low mean atrial pressure
    1. Hypovolemia
    2. Improper zeroing of the transducer
Elevated mean atrial pressure
    1. Intravascular volume overload states
    2. Left ventricular failure due to valvular disease (mitral or aortic stenosis or regurgitation)
    3. Left ventricular failure due to myocardial disease (ischemia or cardiomyopathy)
    4. Left ventricular failure due to systemic hypertension
    5. Pericardial effusion with tamponade physiology
    6. Obstructive atrial myxoma
Elevated $a$ wave (any increase to ventricular filling)
    1. Mitral stenosis
    2. Decreased ventricular compliance due to ventricular failure, aortic valve stenosis, or systemic hypertension
Cannon $a$ wave
    1. Atrial-ventricular asynchrony (atria contract against a closed mitral valve, as during complete heart block following premature ventricular contraction, during ventricular tachycardia, with ventricular pacemaker)
Absent $a$ wave
    1. Atrial fibrillation or atrial standstill
    2. Atrial flutter
Elevated $v$ wave
    1. Mitral regurgitation
    2. Left ventricular heart failure
    3. Ventricular septal defect
$a$ wave equal to $v$ wave
    1. Tamponade
    2. Constrictive pericardial disease
    3. Hypervolemia
Prominent $x$ descent
    1. Tamponade
    2. Subacute constriction and possibly chronic constriction
    3. Right ventricular ischemia with preservation of atrial contractility
Prominent $y$ descent
    1. Constrictive pericarditis
    2. Restrictive myopathies
    3. Mitral regurgitation
Blunted $x$ descent
    1. Atrial fibrillation
    2. Atrial ischemia
Blunted $y$ descent
    1. Tamponade
    2. Ventricular ischemia
    3. Mitral stenosis
Pulmonary capillary wedge pressure not equal to left ventricular end-diastolic pressure
    1. Mitral stenosis
    2. Left atrial myxoma
    3. Cor triatriatum
    4. Pulmonary venous obstruction
    5. Decreased ventricular compliance
    6. Increased pleural pressure
    7. Placement of catheter in a nondependent zone of lung

FIG. 6B

*Pulmonary Artery Pressure Waveforms*

Elevated systolic pressure
    1. Primary pulmonary hypertension
    2. Mitral stenosis or regurgitation
    3. Congestive heart failure
    4. Restrictive myopathies
    5. Significant left to right shunt
    6. Pulmonary disease (pulmonary embolism, chronic obstructive pulmonary disease)

Reduced systolic pressure
    1. Hypovolemia
    2. Pulmonary artery stenosis
    3. Sub- or supravalvular stenosis
    4. Ebstein's anomaly
    5. Tricuspid stenosis
    6. Tricuspid atresia Reduced pulse pressure
    1. Right heart ischemia
    2. Right ventricular infarction
    3. Pulmonary embolism
    4. Tamponade Bifid pulmonary artery waveform
    1. Large left atrial *v* wave transmitted backward (i.e., MR)

Pulmonary artery diastolic pressure greater than pulmonary capillary wedge pressure
    1. Pulmonary disease
    2. Pulmonary embolus
    3. Tachycardia

HEMODYNAMIC WAVEFORM-BASED DIAGNOSIS AND TREATMENT

CROSS-REFERENCE TO RELATED APPLICATIONS

This application is a continuation-in-part of U.S. application Ser. No. 10/698,031, filed Oct. 29, 2003, now U.S. Pat. No. 7,483,743 which claims priority from U.S. Provisional No. 60/470,468, filed May 13, 2003 and which is a continuation-in-part of U.S. application Ser. No. 10/127,227, filed Apr. 19, 2002, now U.S. Pat. No. 7,115,095 which is a continuation of U.S. application Ser. No. 09/956,596, filed Sep. 19, 2001, now abandoned, which is a continuation of U.S. application Ser. No. 09/481,084, filed Jan. 11, 2000, now U.S. Pat. No. 6,328,699, all of which are hereby incorporated by reference. This application also claims priority from U.S. Provisional No. 60/716,611, filed Sep. 13, 2005, which is also incorporated by reference herein.

BACKGROUND OF THE INVENTION

1. Field of the Invention

This invention relates generally to systems and methods for detecting, diagnosing and treating cardiovascular disease in a medical patient.

2. Description of the Related Art

The optimum management of patients with chronic diseases requires that therapy be adjusted in response to changes in the patient's condition. Ideally, these changes are measured by daily patient self-monitoring prior to the development of symptoms. Self-monitoring and self-administration of therapy forms a closed therapeutic loop, creating a dynamic management system for maintaining homeostasis. Such a system can, in the short term, benefit day-to-day symptoms and quality-of-life, and in the long term, prevent progressive deterioration and complications.

In some cases, timely administration of a single dose of a therapy can prevent serious acute changes in the patient's condition. One example of such a short-term disease management strategy is commonly used in patients with asthma. The patient acutely self-administers an inhaled bronchodilator when daily readings from a hand-held spirometer or flowmeter exceed a normal range. This has been effective for preventing or aborting acute asthmatic attacks that could lead to hospitalization or death In another chronic disease, diabetes mellitus, current self-management strategies impact both the short and long term sequelae of the illness. Diabetic patients self-monitor blood glucose levels from one to three times daily and correspondingly adjust their self-administered injectable insulin or oral hypoglycemic medications according to their physician's prescription (known as a "sliding scale"). More "brittle" patients, usually those with juvenile-onset diabetes, may require more frequent monitoring (e.g., 4 to 6 times daily), and the readings may be used to adjust an external insulin pump to more precisely control glucose homeostasis.

These frequent "parameter-driven" changes in diabetes management prevent hospitalization due to symptoms caused by under-treatment (e.g., hyperglycemia with increased hunger, thirst, urination, blurred vision), and over-treatment (e.g., hypoglycemia with sweating, palpitations, and weakness). Moreover, these aggressive management strategies have been shown to prevent or delay the onset of long-term complications, including blindness, kidney failure, and cardiovascular disease.

There are approximately 60 million people in the U.S. with risk factors for developing chronic cardiovascular diseases, including high blood pressure, diabetes, coronary artery disease, valvular heart disease, congenital heart disease, cardiomyopathy, and other disorders. Another 10 million patients have already suffered quantifiable structural heart damage but are presently asymptomatic. Still yet, there are 5 million patients with symptoms relating to underlying heart damage defining a clinical condition known as congestive heart failure (CHF). Although survival rates have improved, the mortality associated with CHF remains worse than many common cancers. The number of CHF patients is expected to grow to 10 million within the coming decade as the population ages and more people with damaged hearts are surviving.

CHF is a condition in which a patient's heart works less efficiently than it should, and a condition in which the heart fails to supply the body sufficiently with the oxygen-rich blood it requires, either during exercise or at rest. To compensate for this condition and to maintain blood flow (cardiac output), the body retains sodium and water such that there is a build-up of fluid hydrostatic pressure in the pulmonary blood vessels that drain the lungs. As this hydrostatic pressure overwhelms oncotic pressure and lymph flow, fluid transudates from the pulmonary veins into the pulmonary interstitial spaces, and eventually into the alveolar air spaces. This complication of CHF is called pulmonary edema, which can cause shortness of breath, hypoxemia, acidosis, respiratory arrest, and death. Although CHF is a chronic condition, the disease often requires acute hospital care. Patients are commonly admitted for acute pulmonary congestion accompanied by serious or severe shortness of breath. Acute care for congestive heart failure accounts for the use of more hospital days than any other cardiac diagnosis, and consumes in excess of 20 billion dollars in the United States annually.

In view of the foregoing, it would therefore be advantageous for a therapeutic device to be able to drive patient therapy with waveforms indicative of various hemodynamic values and parameters.

SUMMARY

In one embodiment, the invention comprises a method of monitoring pressure in an individual. In one embodiment, the method comprises measuring a true or actual pressure in a patient, and measuring one or more indicators of that pressure. In some embodiments, the actual pressure may be difficult to assess or require invasive means. Thus, using an indicator of actual pressure (which may be easier to determine or access) may facilitate determination of actual pressure. By correlating the indicators of actual pressure with the actual pressure during a first given time period, an actual pressure determination in a second given time period can be made by relying solely on the indicator measurement. In this way, actual pressure can be measured in a less-invasive and facile manner.

In other embodiments, a pressure sensor is implanted in a patient. The pressure sensor may be susceptible to drift or inaccuracy over time. By correlating the actual pressure (as determined by the implanted pressure sensor) and one or more indicators of pressure, a correlative relationship (or pre-determined relationship) between the actual pressure and the indicator values may be established. Accordingly, this correlation can be used at a later time to determine if the pressure sensor requires calibration. Alternatively, this correlation can be used to determine actual pressure, even without calibration. The pressure sensor may include the data processing system associated with the sensor.

In one embodiment, a method of monitoring pressure within a medical patient is provided. In one embodiment, the method comprises: measuring an actual pressure in a medical patient in a first time period; measuring an indicator of the actual pressure in the first time period, wherein the indicator is derived from an electrical signal of the patient's heart; determining a correlative relationship between the actual pressure and the indicator, wherein both the actual pressure and the indicator are obtained in the first time period; measuring the indicator in a second time period; and determining the actual pressure in the second time period based on the correlative relationship obtained in the first time period and the indicator obtained in the second time period.

The first time period and second time periods can include any interval of time. Any interval may be selected, such as minutes, hours, days, weeks, months, and/or years, or a combination thereof. Thus, in one embodiment, data regarding actual pressure and indicator value are obtained in a first time period for 1-20 weeks to establish a correlative relationship. The correlation is used in a second time period, which can include the following hours, days, weeks, months or years, after the first time period to calculate an actual pressure based solely on one or more indicator values obtained during the second time period. Alternatively, the indicator data obtained in the second time period may be used to calibrate a pressure sensing device, wherein said calibration can occur automatically or via patient instructions.

The data obtained in the first time period may be considered historical data, such as historical actual pressure data and historical indicator data. Data may include calculations and measurements obtained from one patient or a sampling of several patients. For example, in one embodiment a patient's actual pressure in the second time period is determined based on the relationship between the actual pressure data and indicator data in the first period, wherein that first period data is historical data obtained from one or more other patients. In another embodiment, the historical data is the patient's own data.

The indicator can be selected from a group consisting of one or more of the following: an a-wave, a v-wave, an x-descent, a y-descent, an echocardiogram waveform, and an IEGM waveform. The correlative relationship can be based at least in part on at least one of an amplitude and a timing parameter of the indicator, wherein the indicator is an electrocardiogram signal. In addition, the correlative relationship can comprise an artificial neural network. The determining step can be performed within the medical patient.

In another embodiment, a method of monitoring pressure within a medical patient, comprises: measuring an indicator of a pressure within a medical patient, wherein the indicator is related to an electrical signal generated by a patient; determining the pressure based at least in part upon the indicator and a pre-determined relationship between the pressure and the indicator, wherein the pre-determined relationship is determined from historical pressure data and historical indicator data of the patient; and providing an indication of the pressure.

At least one of the historical pressure data and the historical indicator data can include data from only the medical patent.

In another embodiment, a method of calibrating a pressure monitoring system, comprises: measuring an actual pressure within the heart of a medical patient with a pressure monitoring system; measuring an indicator of the actual pressure, wherein the indicator is related to a physiological parameter of the medical patient; calculating a pressure value indicative of the actual pressure based at least in part upon the indicator of the actual pressure and a pre-determined relationship between the actual pressure and the indicator of the actual pressure, wherein the pre-determined relationship is determined from historical pressure data and historical indicator data of the patient; determining an error value based upon the difference between the measured actual pressure and the calculated pressure value; and calibrating the pressure monitoring system when the error value exceeds a predetermined threshold.

The predetermined relationship can include an artificial neural network. In another embodiment, the actual pressure is a left atrial pressure of a medical patient. In one embodiment, calibrating the pressure monitoring system comprises subtracting the error value from the measured pressure value.

In another embodiment, the method further comprising generating an alert when the error value exceeds the predetermined threshold. In one embodiment, generating an alert comprises providing an instruction to the medical patient to perform a patient calibration procedure. The patient calibration procedure can include performing a Valsalva maneuver. In one embodiment, the calculating is performed within the medical patient.

In yet another embodiment, a method of controlling delivery of a therapy delivered to a patient, comprises: measuring an indicator of an actual pressure within a medical patient, wherein the indicator corresponds to a physiological parameter of the medical patient; determining the actual pressure based at least in part upon the indicator and a pre-determined relationship between the actual pressure and the indicator, wherein the pre-determined relationship comprises a neural network trained with historical pressure data and historical indicator data; and controlling a therapy based upon the determined pressure.

In one embodiment, controlling a therapy comprises controlling at least one device selected from a group consisting of one or more of the following: a cardiac rhythm management device, a defibrillator, a drug infusion system, an ultrafiltration system, an oral drug dose management device, and a diet and activity management device. In another embodiment, controlling a therapy is performed automatically. In yet another embodiment, controlling a therapy comprises providing instructions to a recipient, which can be the medical patient.

In one embodiment, the indicator is selected from a group consisting of one or more of the following: an a-wave, a v-wave, an x-descent, a y-descent, a temperature, a pulmonary artery waveform, a right atrial pressure waveform, a left atrial pressure waveform, an echocardiogram waveform, and an IEGM waveform. In yet another embodiment, the historical pressure data and the historical indicator data are from the patient.

In other embodiments, hemodynamic waveform analysis systems and devices are provided to perform any of the methods described herein. In one embodiment, a hemodynamic waveform analysis device includes an implantable housing, an implantable lead in electrical communication with the housing, and a sensor in communication with the lead. The sensor can include a pressure sensor, an electrical sensor, such as an electrode, a thermometer, an accelerometer, or a flow rate sensor.

In one embodiment, the housing includes a microprocessor, a memory, a data acquisition circuit, and a telemetry circuit. In another embodiment, the housing further includes the circuitry of a pacemaker.

In one embodiment, the microprocessor monitors pressure within a medical patient. In one embodiment, the microprocessor is configured to measure an actual pressure in a medical patient in a first time period; measure an indicator of the actual pressure in the first time period, wherein the indicator is derived from an electrical signal of the patient's heart; determine a correlative relationship between the actual pressure and the indicator, wherein both the actual pressure and the indicator are obtained in the first time period; measure the indicator in a second time period; and determine the actual pressure in the second time period based on the correlative relationship obtained in the first time period and the indicator obtained in the second time period.

In one embodiment, a method of monitoring pressure within a medical patient includes measuring a feature-derived parameter of a pressure; providing an indication of the pressure based at least in part upon a relationship and the feature-derived parameter. The feature-derived parameter can be selected from the group consisting of: an a-wave, a v-wave, an x-descent, a y-descent, a temperature, a pulmonary artery waveform, a right atrial pressure waveform, a left atrial pressure waveform, an echocardiogram waveform, and an IEGM waveform.

In some embodiments, the relationship is based at least in part on an amplitude of the feature-derived parameter, and in other embodiments, the relationship is based at least in part on a timing of the feature-derived parameter. The relationship can include an artificial neural network.

In another embodiment of the present invention, a method of calibrating a pressure monitoring system includes: measuring a pressure with a pressure monitoring system; measuring a feature-derived parameter of the pressure; and calibrating the pressure monitoring system based at least partially upon a relationship between the pressure and the feature-derived parameter of the pressure. In one embodiment, the pressure is a left atrial pressure of a medical patient.

In one embodiment, a system for remote calibration of an implantable medical device includes: a pressure sensor implanted within a medical patient that provides pressure signals; and a processor that analyzes pressure waveforms to determine a calibration based upon a relationship between the pressure signals and a feature-derived parameter of pressure. The feature-derived parameter can be selected from the group consisting of: an a-wave, a v-wave, an x-descent, a y-descent, a temperature, a pulmonary artery waveform, a right atrial pressure waveform, a left atrial pressure waveform, an echocardiogram waveform, and an IEGM waveform.

BRIEF DESCRIPTION OF THE DRAWINGS

FIGS. 6A-6C list examples of signals that may be interpreted to facilitate diagnosis, prevention, and treatment of cardiovascular disease.

DETAILED DESCRIPTION

In one embodiment, waveforms, including those indicative of various hemodynamic values and parameters, are used with therapeutic devices as calibration-independent parameters for diagnostic and surrogate measurements of left atrial pressure ("LAP"). These waveforms can be useful in driving therapy. In other embodiments, devices using waveform feature-derived parameters that are indicative of left atrial pressure and which do not include patient signaling elements drive therapy.

In some embodiments, measurements of LAP are provided based on relative measurements of waveform feature amplitude or timing, and do not use an external atmospheric pressure reference. In other embodiments, measurements of LAP are provided based on relative measurements of waveform feature amplitude or timing, and do not calibrate a pressure sensor zero offset.

In one embodiment, waveform feature-derived parameters or indicators of LAP ("f-LAP") are used by an implantable system to drive or optimize therapy without an external pressure reference. Therapies that can be beneficially controlled include, but are not limited to: cardiac rhythm management, defibrillators, drug infusion systems, ultrafiltration, oral drug dose management, diet and activity management. In some embodiments, therapy is controlled automatically. In other embodiments, therapy is controlled by providing instructions to a patient, a doctor, a medical professional, or other caregiver.

The term "derived," is a broad term that is intended to have its ordinary meaning. In addition, the term "derived," is intended to mean based upon, related to, comes from, or is otherwise produced as a result of.

In one embodiment, a system for remote non-invasive calibration of implantable medical devices analyzes uploaded pressure waveforms to determine sensor calibration. In another embodiment, a system remotely monitors implantable medical devices by analyzing uploaded pressure waveforms to detect either a change in a physiological condition or a miscalibration of a sensor. In yet another embodiment, a system analyzes multiple features of an LAP waveform to provide a signal indicative of the condition of a heart. In one embodiment the system also provides an offset calibration of a pressure sensor. In one embodiment the system does not utilize or require an external pressure reference.

In another embodiment, a classifier, such as an artificial neural network, classifies the condition of a heart based at least in part on the LAP waveform.

Figure 1:
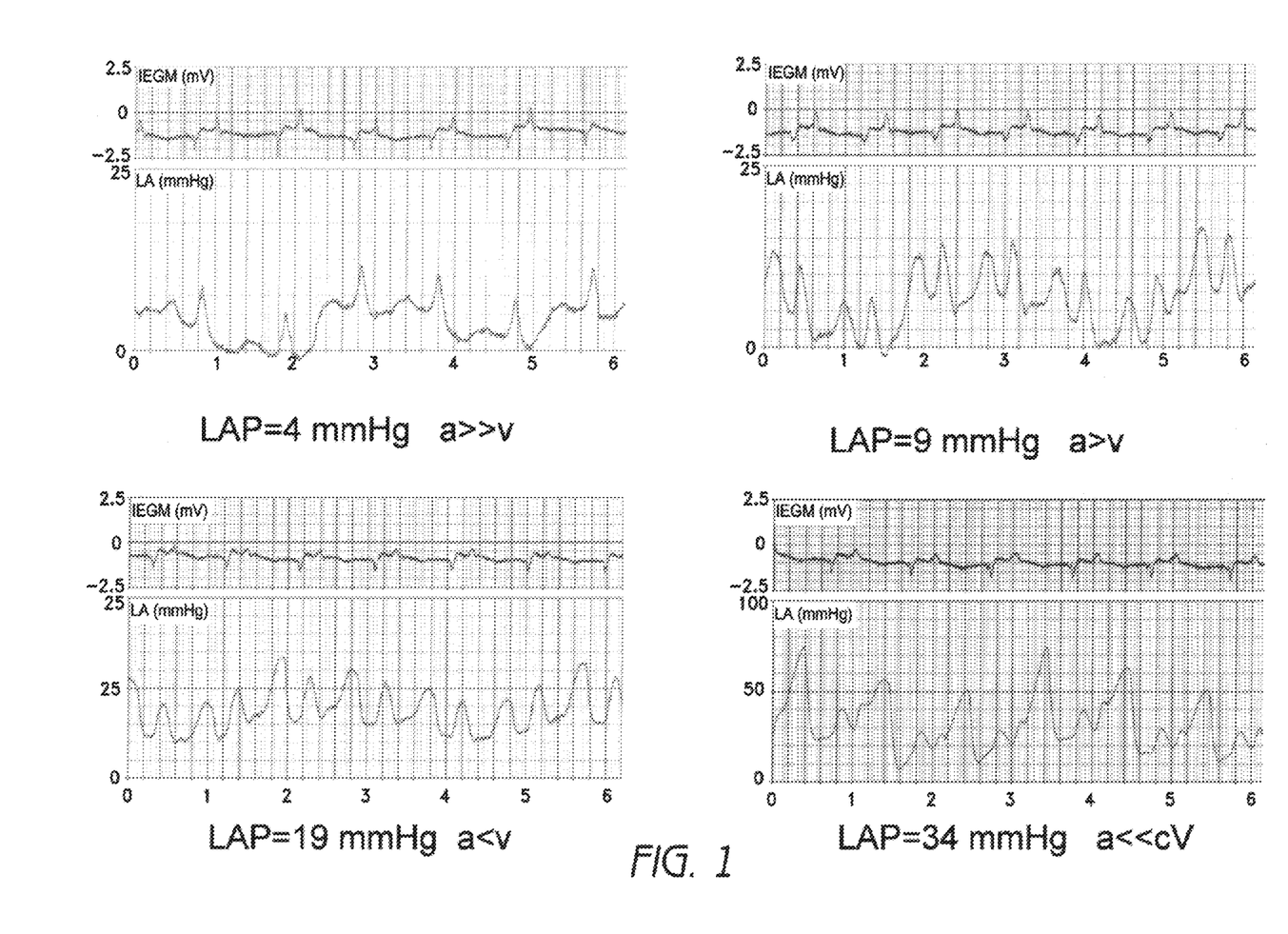
FIG. 1 is a graph of data acquired from an implanted pressure monitoring device in a patient with congestive heart failure.

FIG. 1 shows data acquired from an implanted pressure monitoring device, such as a HeartPOD™, in a patient with congestive heart failure ("CHF"). Simultaneous intra-cardiac electrogram ("IEGM") and LAP pressure waveforms are shown at four different levels of mean LAP, from 4 to 34 mmHg. Changes in features of the pressure waveform are correlated with the mean pressure, demonstrating that such feature changes are indicative of LAP. There is also a linear relationship between the height of the y-descent and the mean LAP. This relationship is illustrated in FIG. 2 below.

Pressure waveforms are measured in any of a variety of ways. For example, pressure waveforms can be generated from pressure transducers that are temporarily positioned or permanently implanted within the body. In some embodiments, pressure is measured with a piezoelectric sensor. In other embodiments, pressure is measured with a pressure transducer that is implanted within a patient's heart. Examples of pressure measuring devices are taught in U.S. application Ser. No. 10/698,031, filed Oct. 29, 2003, Ser. No. 10/127,227, filed Apr. 19, 2002, Ser. No. 10/438,300, filed May 13, 2003, Ser. No. 11/116,138, filed Apr. 27, 2005, and Ser. No. 11/015,336, filed Dec. 17, 2004, which are all incorporated by reference herein.

Figure 2:
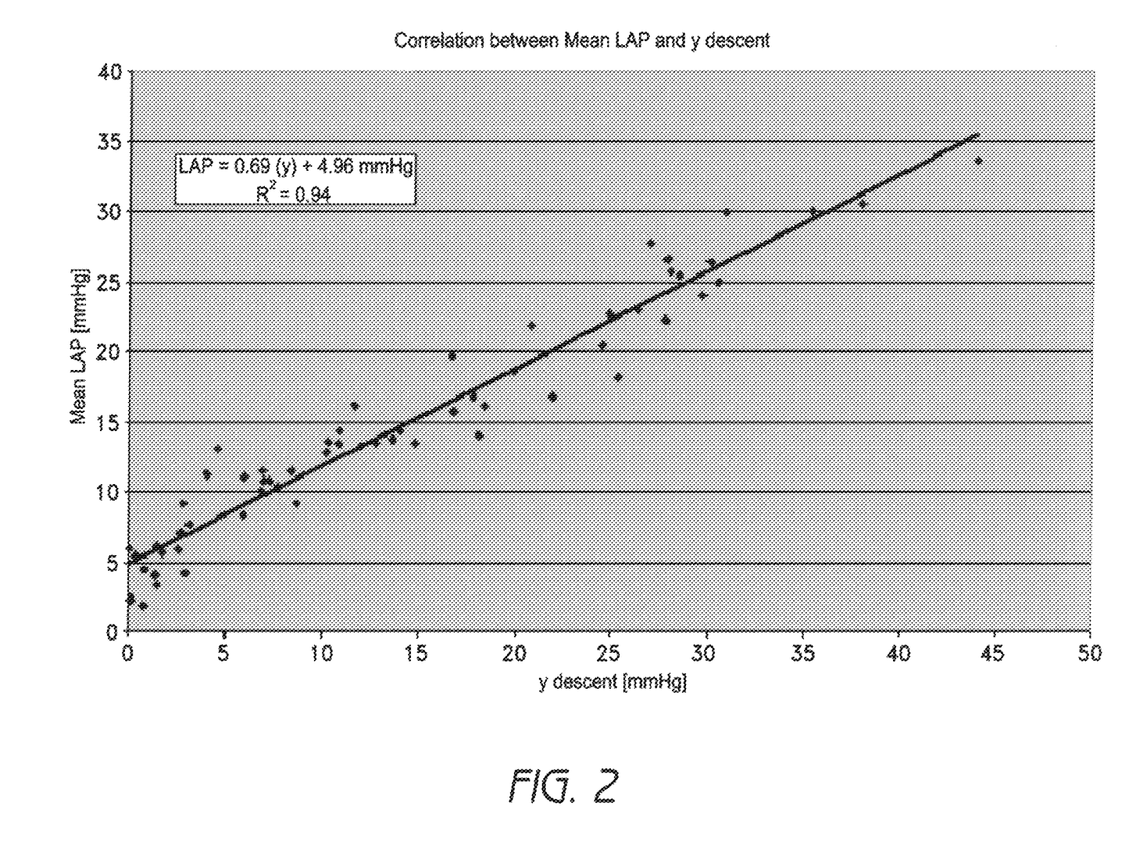
FIG. 2 is a graph of the correlation between mean LAP and the y-descent.

FIG. 2 shows data acquired over the first two weeks after implantation of a left atrial pressure sensor in a patient with congestive heart failure. About four times per day, a 15-second recording of the LAP waveform was acquired with a sampling rate of 200 Hz. For each acquired waveform, the mean left atrial pressure is plotted versus the average height of the y-descent, demonstrating the high degree of correlation between mean of the pressure waveform and the height of one of its features. This high correlation is utilized in several embodiments of the current invention. Data can be acquired during any interval, such as minutes, hours, days, weeks, months, and/or years, or a combination thereof.

In one embodiment, the formula for the mean-LAP vs. y-descent regression line is used to compute an estimate of left atrial pressure from a measurement of the y-descent. It will be clear to one skilled in the art that, unlike the mean LAP, the y-descent can be measured without reference to the external atmospheric pressure. Thus, an index of left atrial pressure based on a relative measurement of a waveform feature, such as the height of the y-descent, has the advantage that it does not require measurement of an external atmospheric pressure reference.

Another advantage of an index of left atrial pressure based on a relative measurement of waveform features is that such measurements are independent of sensor offset calibration. Thus, feature-based relative measurements indicative of left atrial pressure are advantageously unaffected by sensor offset drift. A method and device for measuring left atrial pressure that does not require an atmospheric pressure reference and which is unaffected by pressure sensor drift is particularly advantageous for a permanently implantable pressure measurement system.

In one embodiment of the present invention, a feature-based index of LAP is used as a substitute for mean LAP to diagnose and drive therapy for worsening congestive heart failure. In another embodiment, a feature-based index of LAP is used together with a direct measurement of mean LAP. In one embodiment, the relationship between LAP and f-LAP is used to detect a change in the absolute calibration of the sensor.

The relationship between LAP and the feature-based index (or indicator) of LAP is sometimes referred to as a "correlative relationship," which is a broad term, intended to have its ordinary meaning. In addition, a correlative relationship can include any relationship, such as a formula, a graph, a curve, a linear relationship, a non-linear relationship, a neural network, a classifier, or any other relationship that provides a value of one variable when presented with the value of another variable.

In one embodiment, the difference between LAP and f-LAP is averaged over an interval to determine an offset calibration for the direct LAP measurements. In one embodiment, sudden changes in the relationship between f-LAP and LAP is detected and analyzed. In one embodiment, a sudden change in this relationship is an indication of a change in a physiological condition.

The f-LAP is fundamentally different from other methods and parameters for estimating LAP. For example, f-LAP depends on relative measures of the LAP waveform, and is therefore independent of barometric pressure and sensor offset calibration. Unlike other devices and methods, utilizing f-LAP need not measure pressure relative to a barometric pressure at a specific time in the RV waveform. In addition, in many embodiments, devices and methods utilizing f-LAP do not utilize an atmospheric pressure reference and a sensor with known zero-pressure offset.

Figure 3:
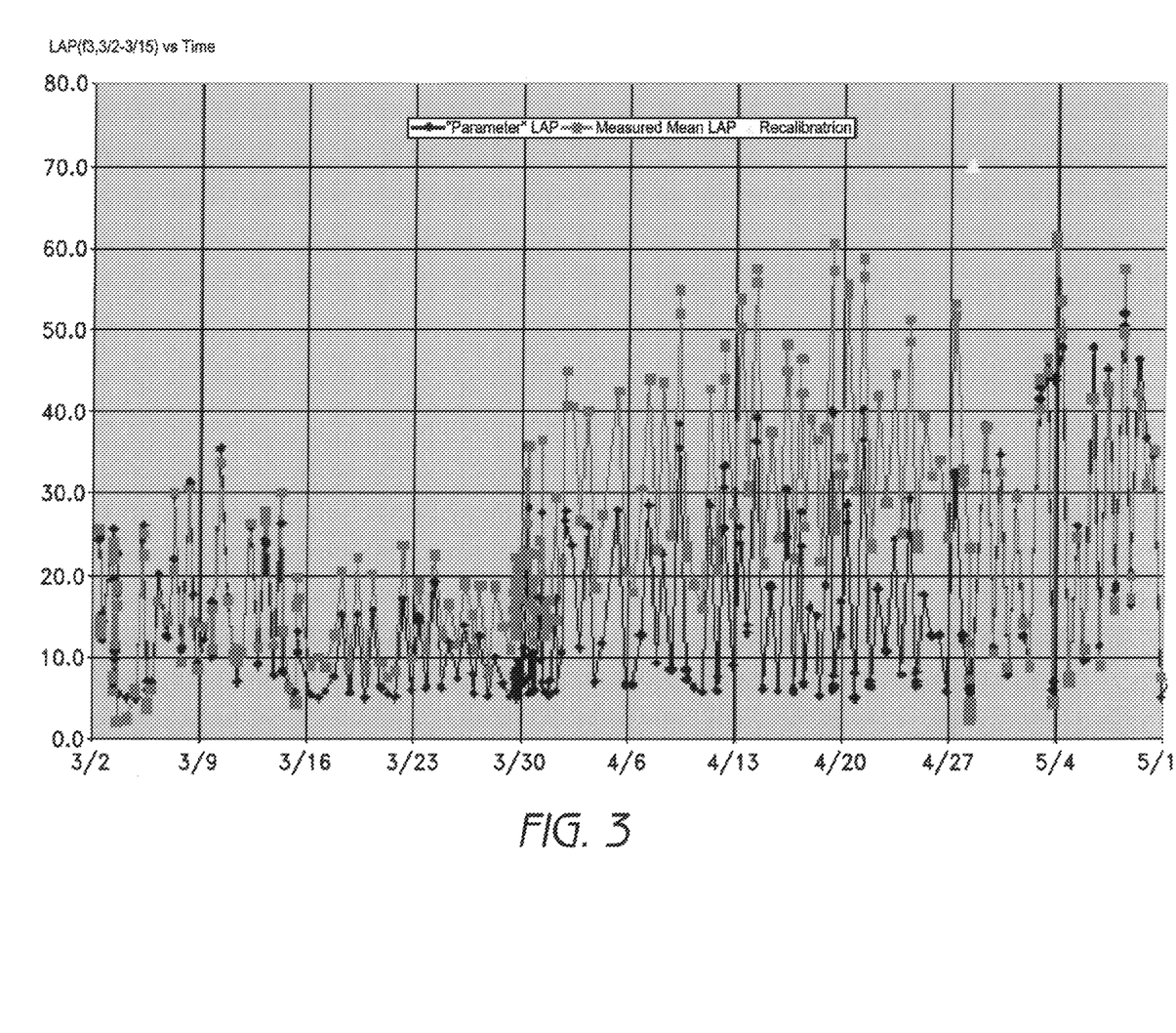
FIG. 3 is a graph of left atrial pressure data over about ten weeks from the same patient.

FIG. 3 shows left atrial pressure data over about 10 weeks from the same patient. The square symbols are direct measurements of mean LAP obtained by averaging sensor output for 15 seconds. The diamonds are feature-based estimates of LAP calculated using a formula that describes the relationship between the height of the y-descent to LAP. The first two weeks includes the same data as in FIG. 2, which was used to determine the relationship between LAP and y-descent in the patient. It is clear that the f-LAP tracks the daily variations in LAP, but that over time the LAP readings can drift higher relative to the f-LAP readings.

Figure 4:
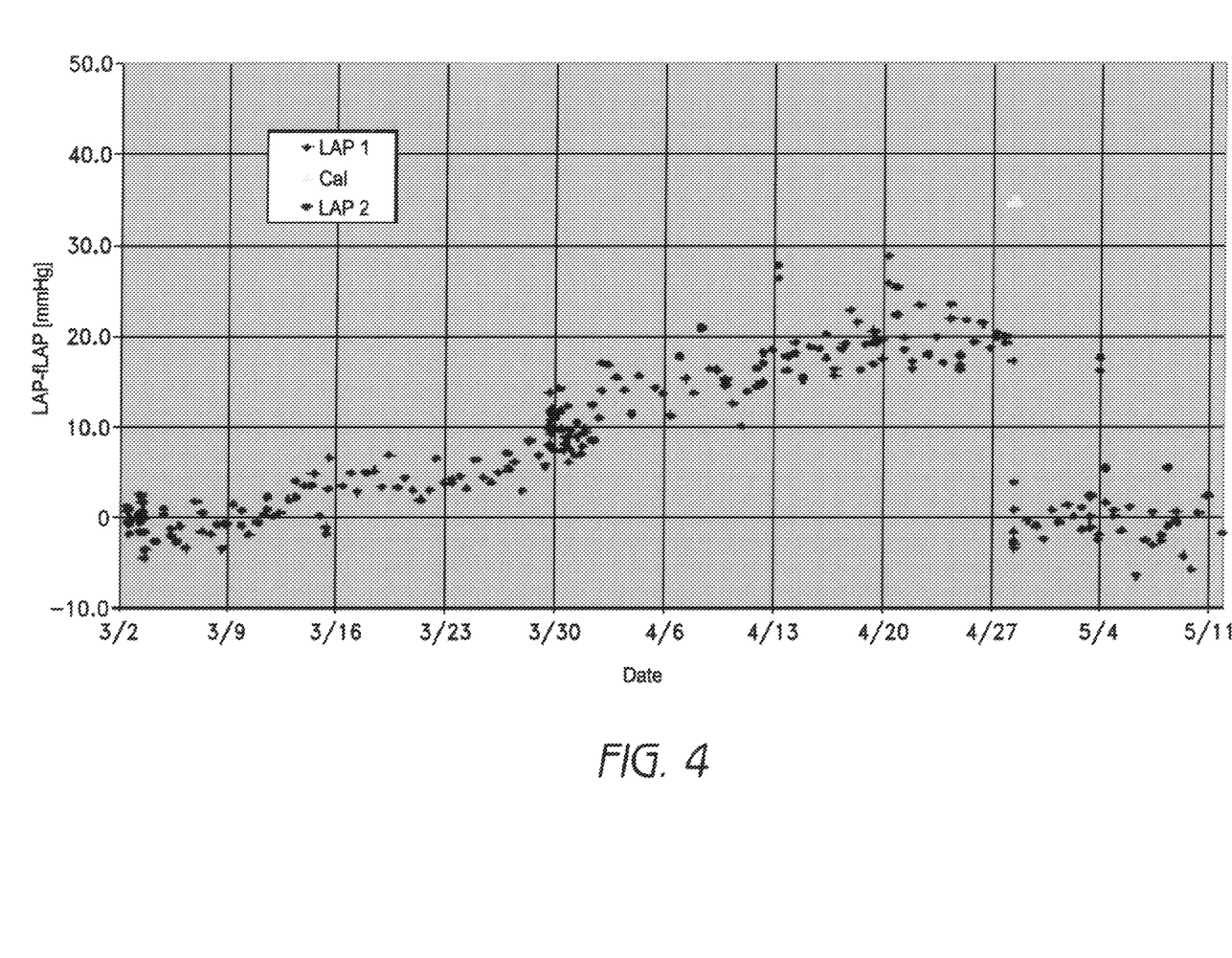
FIG. 4 is a graph of the difference between each LAP and f-LAP reading over the ten-week period post implantation.
Figure 5:
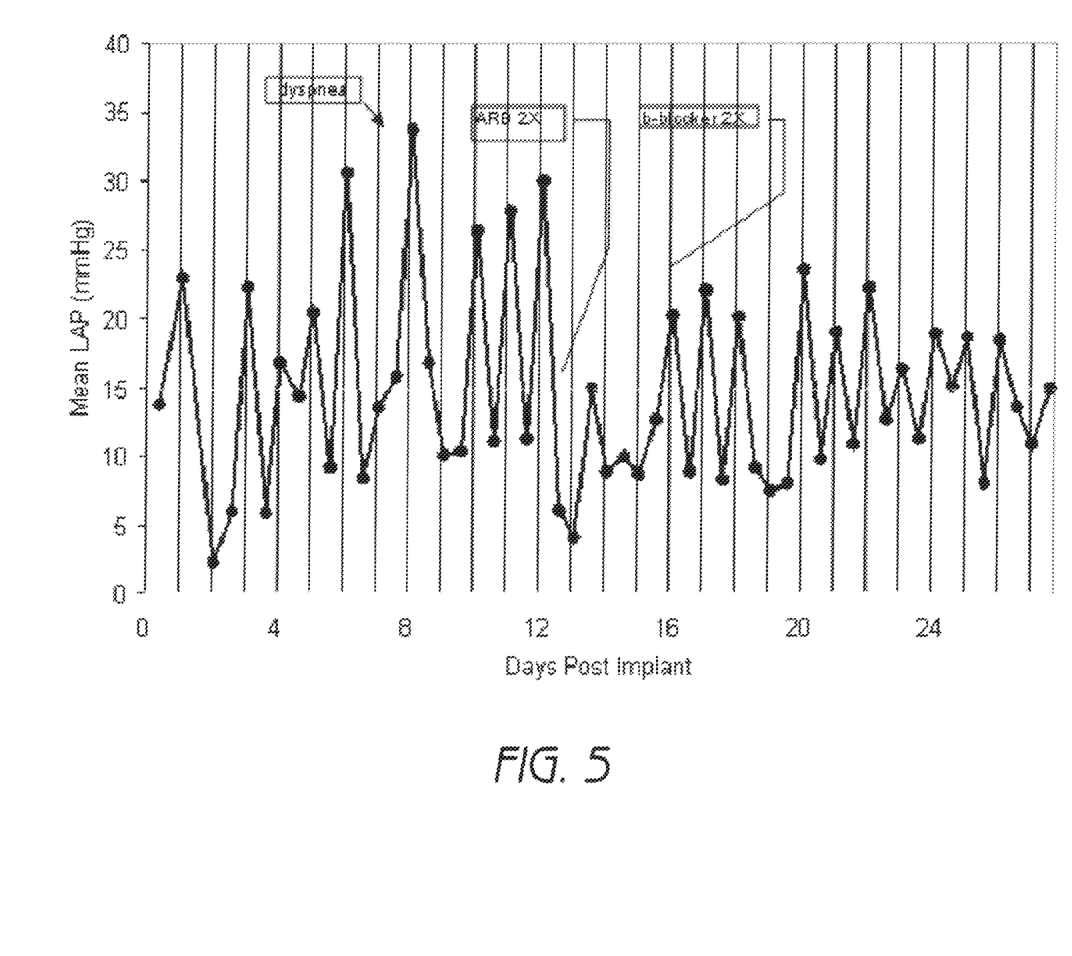
FIG. 5 is a graph of mean LAP post implantation.

FIG. 4 shows the difference between each LAP and f-LAP reading over the 10 weeks after implant, clearly showing this drift. On Apr. 28 Valsalva calibration was performed to determine true LAP. Calibration using a Valsalva maneuver is described in detail in U.S. application Ser. No. 10/438,309, filed May 13, 2003, and U.S. application Ser. No. 10/438,300, filed May 13, 2003, both of which are incorporated by reference herein. The data in FIGS. 3 and 4 both show that this recalibration brings LAP and f-LAP back into agreement, demonstrating that f-LAP accurately predicts mean LAP, and that the difference between mean LAP and f-LAP is an accurate measure of LAP sensor offset, which may be referred to as an error value.

In one embodiment of the present invention, the difference between LAP and an f-LAP is used to perform sensor calibration. In one such embodiment, the difference is averaged over a number of measurements or over an interval of time to derive an offset correction. In one embodiment the interval of time is one week, and an offset correction is applied to the sensor LAP readings each week. In another embodiment, the interval is one month, or some other interval that may be chosen by the patient's physician. In another embodiment, the interval is one week, and a new calibration is applied each day based on the most recent seven-day average difference. Any interval may be selected, such as minutes, hours, days, weeks, months, and/or years, or a combination thereof.

Figure 6C:
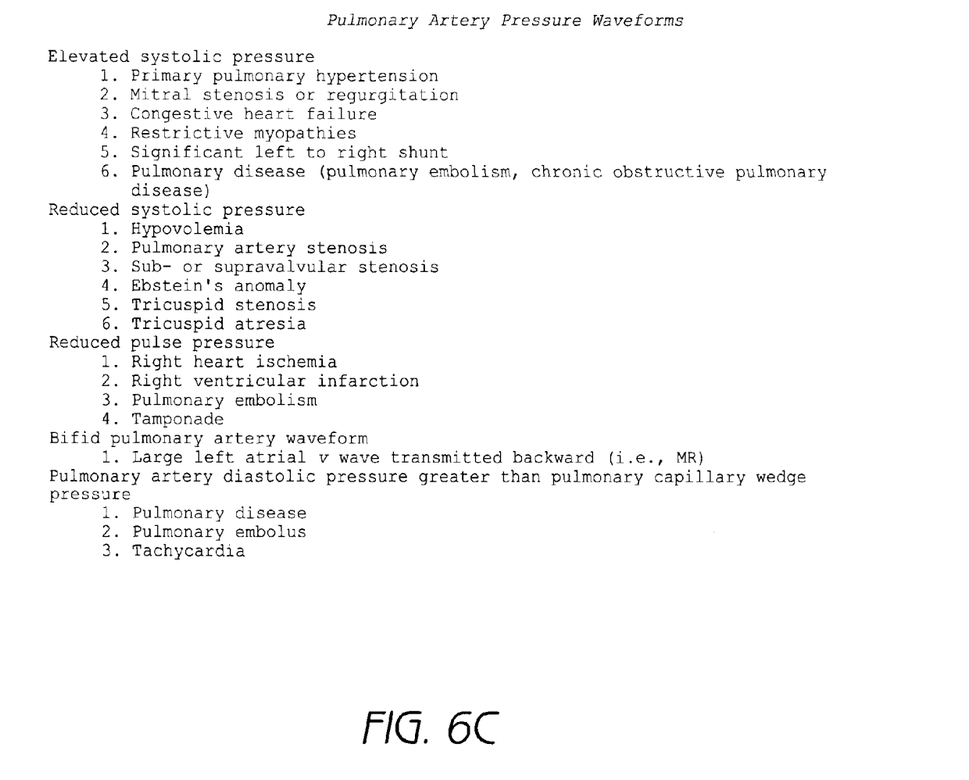
Figure 7:
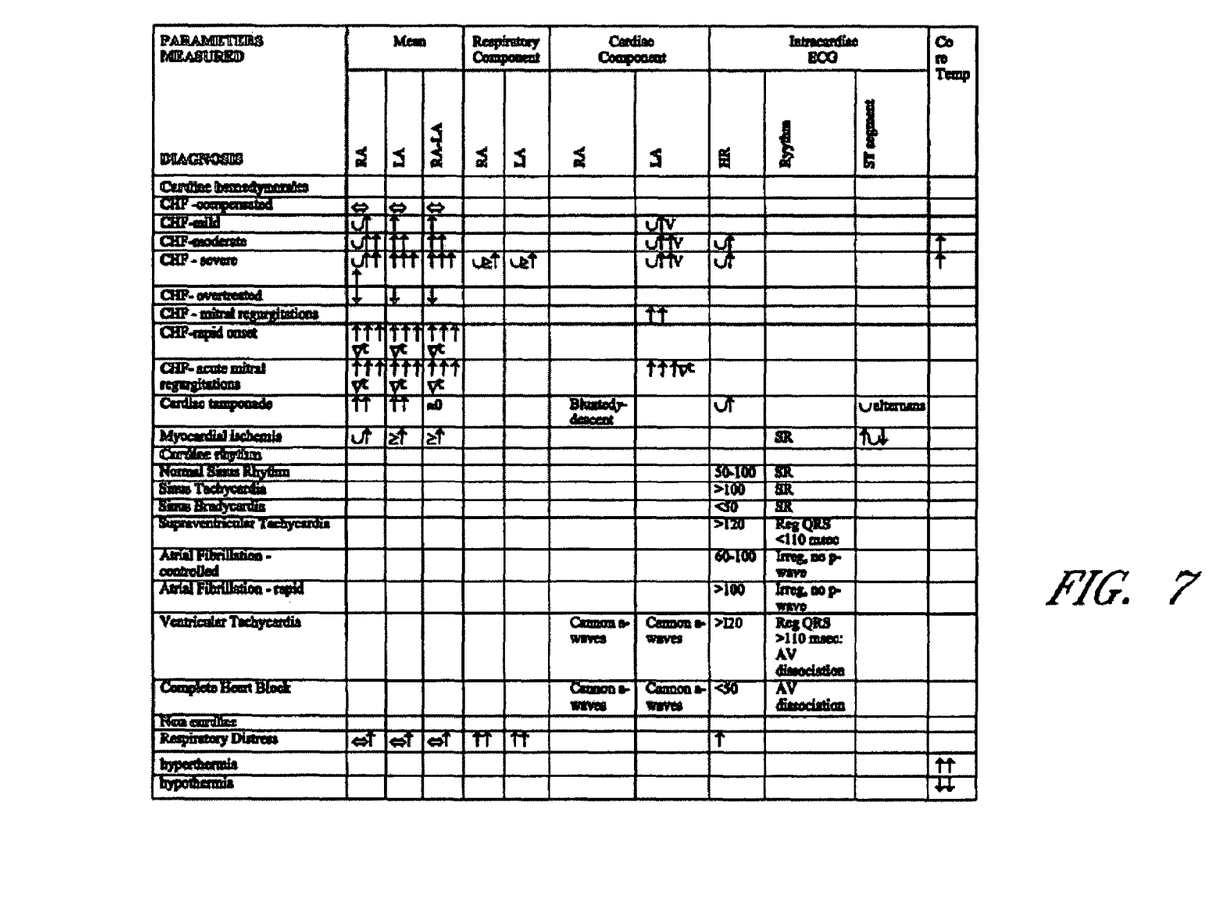
FIG. 7 is a table of cardiac and non-cardiac diagnostic states derivable from hemodynamic measurements.

It is known to those of skill in the art that the relationship between a mean cardiac pressure measurement and a waveform feature measurement also may be affected by physiological changes. A list of examples of pressure waveform features and corresponding physiological conditions is provided in FIGS. 6A-6C. Examples of cardiac and non-cardiac diagnostic states derivable from measurements at the intra-atrial septum are shown in FIG. 7 of the same application.

In several embodiments of the present invention, the systems, devices and methods employed distinguish between a change in physiological condition and a change in sensor calibration. In one embodiment of the present invention, the difference between LAP and an f-LAP is monitored as described above to derive an offset correction, but the offset correction is not always automatically applied. Instead, a calibration alert is generated whenever the correction derived from the LAP versus f-LAP difference exceeds a predetermined threshold. In one embodiment, the interval of time is one week and an offset correction is calculated once a week. In another embodiment, the interval is one week and the offset correction is calculated each day based on the most recent seven-day average difference. In another embodiment, the interval is one month. Any interval may be selected, such as minutes, hours, days, weeks, months, and/or years, or a combination.

In one embodiment, the alert includes an instruction to the patient to perform a calibration, such as a Valsalva calibration. In one embodiment, the patient is further instructed to contact his or her physician if the calibration, such as a Valsalva calibration, does not bring LAP and f-LAP into agreement. In another embodiment, the alert includes an instruction to the patient to go to the physician's office to perform a calibration so that the physician can evaluate whether the discordance between LAP and f-LAP is physiological or sensor drift. In another embodiment, two or more LAP feature parameters are analyzed, and the combination of parameters is used to distinguish between various physiological changes (such as those as shown in FIG. 7), and between physiological changes and sensor calibration changes using this approach.

Although it is known in the art to recognize various conditions of a heart based on parameters of left atrial pressure (such as the conditions and parameters described in FIG. 7), a more comprehensive classification of waveform morphologies according to corresponding physiological conditions can be achieved by training an artificial neural network (ANN) to do the classification.

As is known in the ANN arts, an ANN generally includes one or more training sets of input/output pairs. In one embodiment, the training sets include waveforms and known corresponding physiological conditions. The training sets can include the entire waveform, or one or more parameters derived from the waveform, such as the height of the y-descent discussed above. In one embodiment, the ANN is provided or trained with both an LAP waveform and an IEGM waveform. In another embodiment, the ANN is provided or trained with parameters of the IEGM, for example the heart rate and the p-r interval, and the relative pressure values and timing of the maxima and minima in the corresponding LAP waveform.

In one embodiment the ANN output includes a mean LAP and a physiological condition. In one embodiment the physiological condition is one of: tamponade, mitral regurgitation, atrial fibrillation, constrictive pericarditis, as well as all of the conditions listed in FIGS. 6A-6C and FIG. 7.

In one embodiment, an ANN is trained using waveforms and conditions for a single patient and is used to analyze the data from only that patient. Such a restriction improves the accuracy of the ANN for a given number of training pairs because of the reduced variability in input waveforms from a single patient. In another embodiment, an ANN is trained and used for classifying waveforms from any patient, or from any of a particular group or class of patient.

In one embodiment of the present invention, the analysis required to calibrate an implanted pressure sensor based on LAP waveform parameters includes identifying the relevant feature or features within the LAP pressure waveform, measuring the appropriate feature parameter or parameters, and computing the f-LAP from the feature parameters, and subtracting the f-LAP values from the mean LAP to derive the offset calibration. In one embodiment, this analysis is performed by an external patient advisory module ("PAM").

In another embodiment, the analysis is performed by a computer, which is particularly advantageous when the algorithms for identification of features and/or measurement of parameters are complex. In one embodiment, waveforms stored in the PAM are uploaded to a computer, which can be located in the patient's home. If the calculated offset calibration differs from the current calibration, in one embodiment the computer downloads the new calibration to the PAM. In another embodiment the patient is notified to calibrate, and the patient may be instructed to contact the physician, or the patient may be instructed to perform a Valsalva calibration as described above.

In another embodiment, the computer is located in the doctor's office, and waveforms from the patient's PAM are uploaded, and a new calibration is downloaded, such as during an office visit. In another embodiment, the computer performing the waveform analysis may be remote from the patient, and the patient uploads data from the PAM telemetrically, for example via a telephone modem or an internet connection, as is well known to those skilled in the art. In such embodiments, the remote computer can be located at the doctor's office, or at a central site configured to receive and process calibration data from multiple patients' implanted devices.

In one embodiment, the uploaded data includes raw LAP waveform data, simultaneously acquired IEGM waveforms, and current calibration factors. The remote computer performs f-LAP analysis to determine a new calibration. If the PAM requires a calibration change, the new calibration based on the parameters of the telemetrically uploaded waveforms may be downloaded telemetrically to the PAM, providing a system for remote calibration of implanted medical devices. In another embodiment, the patient and/or the doctor are notified that a re-calibration is required.

What is claimed is:

1. A method of monitoring pressure within a medical patient, comprising:
    measuring an actual pressure in a medical patient in a first time period;
    measuring an indicator of said actual pressure in the first time period, wherein said indicator is derived from an electrical signal of the patient's heart;
    determining by electronic hardware, a correlative relationship between the actual pressure and the indicator, wherein both the actual pressure and the indicator are obtained in the first time period;
    measuring the indicator in a second time period; and
    determining the actual pressure in said second time period based on the correlative relationship obtained in said first time period and the indicator obtained in said second time period.

2. The method of claim 1, wherein the indicator is selected from a group consisting of one or more of the following: an echocardiogram waveform, and an IEGM waveform.

3. The method of claim 1, wherein the correlative relationship is based at least in part on at least one of an amplitude and a timing parameter of the indicator, wherein said indicator is an electrocardiogram signal.

4. The method of claim 1, wherein the correlative relationship comprises an artificial neural network.

5. The method of claim 1, wherein said determining is performed within the medical patient.

6. The method of claim 1, wherein the electronic hardware comprises a processor.

7. The method of claim 1, wherein the measuring an actual pressure, an indicator of said actual pressure, and the indicator in a second time period, and the determining the actual pressure are implemented by the electronic hardware.

8. The method of claim 1, wherein the measuring an indicator of said actual pressure is implemented with an electrode.

9. A method of monitoring pressure within a medical patient, comprising:
- measuring an indicator of a pressure within a medical patient, wherein the indicator is related to an electrical signal generated by the patient;
- determining by electronic hardware the pressure based at least in part upon the indicator and a pre-determined relationship between the pressure and the indicator, wherein the pre-determined relationship is determined from historical pressure data and historical indicator data of the patient; and
- providing an indication of the pressure.

10. The method of claim 9, wherein at least one of said historical pressure data and said historical indicator data comprises data from only said medical patent.

11. The method of claim 9, wherein the electronic hardware comprises a processor.

12. The method of claim 9, wherein the measuring an indicator of a pressure and providing an indication of the pressure are implemented by the electronic hardware.

13. The method of claim 9, wherein the measuring an indicator of a pressure is implemented with an electrode.

* * * * *

UNITED STATES PATENT AND TRADEMARK OFFICE
CERTIFICATE OF CORRECTION

| | |
|---|---|
| PATENT NO. | : 8,298,150 B2 |
| APPLICATION NO. | : 11/520454 |
| DATED | : October 30, 2012 |
| INVENTOR(S) | : Mann et al. |

It is certified that error appears in the above-identified patent and that said Letters Patent is hereby corrected as shown below:

In the Drawings:

Sheet 6 of 9 (Fig 6A) at line 33, change "myopathv" to --myopathy--.

Sheet 9 of 9 (Col. 10, Row 2, Fig. 7) at line 1, change "Ryythm" to --Rhythm--.

In the Specification:

In column 1 at line 47, change "death" to --death.--.

In column 3 at line 59, change "patent." to --patient.--.

In the Claims:

In column 12 at line 3, in claim 10, change "patent." to --patient.--.

Signed and Sealed this
Ninth Day of April, 2013

Teresa Stanek Rea
*Acting Director of the United States Patent and Trademark Office*